(12) United States Patent
Makwana et al.

(10) Patent No.: US 11,667,947 B2
(45) Date of Patent: Jun. 6, 2023

(54) SYSTEMS AND METHODS FOR EVALUATING THE EFFICACY OF ANTI-PATHOGENIC AGENTS AND COMPOSITIONS COMPRISING SAME

(71) Applicant: Colgate-Palmolive Company, New York, NY (US)

(72) Inventors: Ekta Makwana, Monroe, NJ (US); Carlo Daep, Brooklyn, NY (US)

(73) Assignee: Colgate-Palmolive Company, New York, NY (US)

( * ) Notice: Subject to any disclaimer, the term of this patent is extended or adjusted under 35 U.S.C. 154(b) by 474 days.

(21) Appl. No.: 16/704,052

(22) Filed: Dec. 5, 2019

(65) Prior Publication Data
US 2020/0199643 A1 Jun. 25, 2020

Related U.S. Application Data

(60) Provisional application No. 62/782,648, filed on Dec. 20, 2018.

(51) Int. Cl.
| | |
|---|---|
| *C12Q 1/18* | (2006.01) |
| *G16B 40/10* | (2019.01) |
| *C12Q 1/02* | (2006.01) |
| *C12Q 1/24* | (2006.01) |
| *G06F 17/15* | (2006.01) |

(52) U.S. Cl.
CPC .............. *C12Q 1/18* (2013.01); *C12Q 1/025* (2013.01); *C12Q 1/24* (2013.01); *G06F 17/15* (2013.01); *G16B 40/10* (2019.02)

(58) Field of Classification Search
CPC ............. C12Q 1/18; C12Q 1/025; C12Q 1/24
See application file for complete search history.

(56) References Cited

U.S. PATENT DOCUMENTS 5,654,165 A * 8/1997 Kusunoki ............... C12Q 1/18
435/286.4

OTHER PUBLICATIONS

Kiamco et al. 2017 (Hyperosmotic Agents and Antibiotics Affect Dissolved Oxygen and pH Concentration Gradients in *Staphylococcus aureus* Biofilms; Applied and Environmental Microbiology, 83: e02783-16) (Year: 2017).*
Wolcott et al. 2012 (The Polymicrobial Nature of Biofilm Infection; Clin Microbiol Infect 19: 107-112). (Year: 2012).*
Manus et al. 2018 (Enhanced In Vitro Zinc Bioavailability through Rational Design of a Dual Zinc plus Arginine Dentrifrice; J Clin Dent 29(Spec Iss A):A10-19). (Year: 2018).*
Agilent Technologies, Inc., 2018, "Seahorse XFe Analyzer Operating Manual," Second Edition www.agilent.com.
Lamprecht et al., 2016, "Turning the respiratory flexibility of *Mycobacterium tuberculosis* against itself," Nature Communications 7:12393.
Lobritz et al., 2015, "Antibiotic efficacy is linked to bacterial cellular respiration," Proceedings of the National Academy of Sciences 112(27):8173-8180.
Saini et al., 2016, "Ergothioneine maintains redox and bioenergetic homeostasis essential for drug susceptibility and virulence of *Mycobacterium tuberculosis*," Cell Reports 14:572-585.
Seahorse Bioscience, 2016, "Seahorse XFe Extracellular Flux Analyzers: The World's Most Advanced Metabolic Analyzers," www.seahorsebio.com.
Anonymous, "Measuring Cell Metabolism-Transient Mocro-Chamber Video", retrieved on Jul. 6, 2020 <https://www.agilent.com/en/products/cell-analysis/seahorse-analyzers/cell-analysis-measuring-cell-metabolism-transient-micro-chamber>.
International Search Report and the Written Opinion of the International Searching Authority issued in International Application PCT/US2019/064590 dated Mar. 25, 2020.
Kiamco et al., "Hyperosmotic Agents and Antibiotics Affect Dissolved Oxygen and pH Concentration Gradients in *Staphylococcus aureus* Biofilms", Applied and Environmental Microbiology, 83(6):1-13 (2017).
Ludensky, ML, "An automated system for biocide testing on biofilms", Journal of Industrial Microbiology and Biotechnology, 20(2):109-115 (1998).
Madlena et al., "Effect of Amine Flouride/Stannous Flouride Toothpaste and Mouthrinse on Dental Plaque Accumulation and Gingival Health", Oral Diseases, 10(5):294-297 (2004).
Manus et al., "Enhanced in Vitro Zinc Bioavailability through Rational Design of a Dual Zinc plus Arginine Dentifrice", The Journal of Clinical Dentistry, 29(3):A10-A19 (2018).
Preston et al., "Screening of the 'Pathogen Box' identifies an approved pesticide with major anthelmintic activity against the barber's pole worm", International Journal for Parasitology: Drugs and Drug Resistance, 6(3):329-334 (2016).
Solokhina et al., "Drug susceptibility testing of Mature *Mycobacterium tuberculosis* H37Ra and *Mycobacterium smegmatis* Biofilms with Calorimetry and Laser Spectroscopy", Elsevier, 113:91-98 (2018).

* cited by examiner

*Primary Examiner* — Mary Maille Lyons

(57) ABSTRACT

Described herein are methods and systems for identifying a composition having anti-pathogenic activity; evaluating the anti-pathogenic activity of a composition; measuring the metabolic function of a pathogen; and/or comparing the anti-pathogenic performance of a plurality of compositions.

13 Claims, No Drawings

SYSTEMS AND METHODS FOR EVALUATING THE EFFICACY OF ANTI-PATHOGENIC AGENTS AND COMPOSITIONS COMPRISING SAME

CROSS-REFERENCE TO RELATED PATENT APPLICATION

The present application claims the benefit of priority from U.S. Provisional Application No. 62/782,648, filed Dec. 20, 2018, the contents of which are hereby incorporated herein by reference, in their entirety.

BACKGROUND

Bacterial cells secrete toxins and produce inflammation that are associated with health related issues, such as septic shock, fever and malaise. Oral care compositions may comprise anti-microbial or anti-pathogenic agents to hinder the bio-activity of such bacterial cells, thereby preventing the transfer of such toxins to a user. However, difficulty exists in accurately determining the efficacy of anti-microbial or anti-pathogenic agents and compositions comprising same. As a result, it is a challenge for formulators to determine the type and/or concentration of an anti-microbial agent needed to impart the desired anti-microbial effect in an oral care composition. Accordingly, a need exists to determine the anti-microbial activity of anti-microbial agents in oral care compositions.

Embodiments of the present inventions are designed to meet these, and other, ends.

BRIEF SUMMARY

In some embodiments, the present invention provides a method for identifying a composition having antimicrobial activity comprising: a) providing a bacterial biofilm; b) preparing a suspension comprising the bacterial biofilm; c) preparing a first mixture comprising the suspension comprising the bacterial biofilm, a test composition and media for culturing the bacterial biofilm; d) preparing a second mixture comprising the suspension comprising the bacterial biofilm, a control composition and media for culturing the bacterial biofilm; e) measuring the oxygen consumption rate and/or extracellular acidification rate of the first mixture and the second mixture; and f) comparing: (i) the oxygen consumption rate of the first mixture to the oxygen consumption rate of the second mixture; and/or (ii) the extracellular acidification rate of the first mixture to the extracellular acidification rate of the second mixture; wherein when the first mixture provides: a lower oxygen consumption rate compared to the second mixture; or a lower extracellular acidification rate compared to the second mixture, the test composition is identified as having antimicrobial activity.

Other embodiments provide systems for: identifying a composition having anti-pathogenic activity; evaluating the anti-pathogenic activity of a composition; measuring the metabolic function of a pathogen; and/or comparing the anti-pathogenic performance of a plurality of compositions; wherein the system comprises: a specimen comprising a pathogen; a test sample comprising the specimen, a test composition and media for culturing the specimen; a control sample comprising the specimen, a control composition and media for culturing the specimen; a plurality of microwell plates; and an apparatus comprising: at least one optical sensor; and a processor.

Further embodiments of the present invention provide methods for evaluating the antimicrobial activity of a composition comprising: a) providing a multi-species bacterial biofilm; b) preparing a suspension comprising the bacterial biofilm; c) providing a test composition and a control composition; d) providing media for culturing the bacterial biofilm; e) preparing a first mixture comprising the suspension comprising the bacterial biofilm, the test composition and the media for culturing the bacterial biofilm; f) preparing a second mixture comprising the suspension comprising the bacterial biofilm, the control composition and the media for culturing the bacterial biofilm; and g) measuring the oxygen consumption rate and/or extracellular acidification rate of the first mixture and the second mixture.

Further areas of applicability of the present invention will become apparent from the detailed description provided hereinafter. It should be understood that the detailed description and specific examples, while indicating the preferred embodiment of the invention, are intended for purposes of illustration only and are not intended to limit the scope of the invention.

DETAILED DESCRIPTION

The following description of the preferred embodiment(s) is merely exemplary in nature and is in no way intended to limit the invention, its application, or uses.

As used throughout, ranges are used as shorthand for describing each and every value that is within the range. Any value within the range can be selected as the terminus of the range. In addition, all references cited herein are hereby incorporated by referenced in their entireties. In the event of a conflict in a definition in the present disclosure and that of a cited reference, the present disclosure controls.

Unless otherwise specified, all percentages and amounts expressed herein and elsewhere in the specification should be understood to refer to percentages by weight. The amounts given are based on the active weight of the material.

According to the present application, the term "about" means +/−5% of the reference value. According to the present application, the term "substantially free" less than about 0.1 wt. % based on the total of the referenced value.

In some embodiments, the present invention is directed to methods of assessing the activity of an anti-microbial agent in an oral care composition. In some embodiments, the methods utilize a placebo as a control composition. In some embodiments, the oral care composition is in a form a selected from a toothpaste; a gel; a prophy; a mouthwash or mouth rinse; and an orally dissolving tablet.

As used herein, the terms "anti-bacterial" and "anti-microbial" may be used interchangeably, to refer to inhibiting bacterial or microbial growth and/or metabolization.

As used herein, the term "anti-pathogenic" refers to the ability of an agent to kill or inhibit or retard the growth or proliferation of a pathogen.

In some embodiments, the present invention provides a system for assessing one or more anti-microbial agents. In some embodiments, the system comprises an apparatus comprising one or more sensors. In some embodiments, at least one of the one or more sensors is an optical sensor. In other embodiments, the system may further comprise one or more central processing units ("CPUs") for analyzing the data gathered by the sensors.

In some embodiments, the methods and systems described herein may comprise a sample comprising a pathogen. In certain embodiments, the sample may comprise a bacterium cultured with a saccharide, thereby allowing the bacterium to perform cellular respiration by utilizing glycolysis to metabolize the saccharide and produce energy. As the bacteria metabolizes the saccharide, the one or more sensors contact a test composition, whereby the sensors may be configured to gather data on oxygen consumption rate (herein referred to as "OCR") and/or extracellular acidification rate ("ECAR") of the bacteria in the test composition. The OCR and/or ECAR information gathered by the sensor may be transmitted to the CPU for further data processing and/or storage.

OCR corresponds to cytoplasmic respiration of a bacterial cell or mitochondrial respiration of a fungal cell. Specifically, the cytoplasm of the bacteria consumes oxygen when oxidizing fatty acids or other substrates (such as sugars) to generate ATP. In some embodiments, the systems of the present invention use sensors to measure the mitochondrial respiration by measuring the oxygen consumption rate (OCR) of bacterial cells. In some embodiments, reductions in the measured OCR versus a control is indicative of bacterial activity. For instance, decreasing OCR over time indicates a reduction in bacterial viability, and increasing OCR over time indicates an increase in bacterial viability.

ECAR corresponds to cells generating ATP via glycolysis independent of oxygen and producing lactic acid and protons. In some embodiments, the systems of the present invention use sensors to also independently measure the extracellular acidification rate (ECAR) of the bacterial cells—i.e., the rate at which acid is produced. In some embodiments, differences in measured ECAR versus a control is indicative of bacterial activity. For instance, decreasing ECAR over time may indicate a reduction in bacterial viability; and increasing ECAR over time may indicate an increase in bacterial viability.

In some embodiments, the systems comprise an evaluation apparatus. In other embodiments, the system may be calibrated such that measurements are outputted within a sensitivity limit of the evaluation apparatus. In addition to that, the present invention may also allow for specific calibration for each sample tested.

In some embodiments, the methods comprise a harvesting step. In some embodiments, the harvesting step may comprise culturing at least one oral biofilm from an unbrushed saliva inoculum. The biofilms may be cultured on hydroxyapatite disk and supplemented with at least one of hemin, menadione, and at least one saccharide. The saccharide may be selected from a monosaccharide, a polysaccharide, and a combination thereof. In a non-limiting example, the monosaccharide may be sucrose. In further embodiments, the resulting biofilms are collected in water to form a bacterial suspension.

In some embodiments, a first sample is prepared by filling a first container with a first volume of the bacterial suspension. In some embodiments, a second sample may be prepared according to a mixing step, whereby a second container is filled with a second volume of the bacterial suspension and at least one anti-microbial agent. While the second sample comprises an anti-microbial agent, the first sample may be substantially free of any anti-microbial agent—thereby providing the placebo for comparison. Non-limiting examples of anti-microbial agents include zinc citrate, zinc oxide, tin, a basic amino acid (e.g. arginine) and the like.

With a sensor contacting each of the first and second samples, the bacteria present in each sample is allowed to continue to metabolize the saccharide—during which the $OCR_0$, $OCR_1$ of each sample is continually measured. The $OCR_0$ measurement of the first sample and the $OCR_1$ measurement of the second sample may occur for a predetermined time period, referred to as a measurement cycle. The measurement cycle of the first sample may be equal to the measurement cycle of the second sample.

The number of measurement cycles for each sample may be a predetermined. The span of each cycle may range from about 1 second up to about 600 seconds—including all times and sub-ranges therebetween. The number of cycles may range from about 1 to about 99—including any integer and sub-range therebetween. The span and number of cycles may be selected such as to observe a notable change in OCR over time for at least one of the first and second samples. the span and number of cycles may be selected such as to observe a notable change in ECAR over time for a test sample and a control sample.

Once $OCR_0$, $OCR_1$ values for the test sample(s) and control sample(s) are collected, the CPU may perform a data analysis on recorded values and generate a comparison in difference of oxygen consumption rate for the sample containing the anti-bacterial agent and the sample that is a placebo. The OCR comparison may indicate a reduction in $OCR_1$ over time for the sample containing an antibacterial agent, compared to $OCR_0$ for the placebo or control sample over the same time period, indicating that metabolic function slowed in the presence of the anti-microbial agent, thereby confirming the efficacy of the anti-microbial agent, above and beyond any placebo effect.

Alternatively, the OCR comparison may indicate no or substantially no reduction in $OCR_1$ over time for the sample containing the antibacterial agent compared to $OCR_0$ for the placebo or control sample over the same time period, indicating that the metabolic function was not reduced or inhibited by the presence of an anti-microbial agent.

Once $ECAR_0$, $ECAR_1$ values for the first and second samples are collected, the CPU may perform a data analysis on recorded values and generate a comparison in difference of extracellular acidification rate for the second sample containing the anti-bacterial agent and the first sample that is a placebo. The ECAR comparison may indicate a reduction in $ECAR_1$ over time for the second sample compared to $ECAR_0$ for the first sample over the same time period, indicating that the metabolization of the bacterial sample slowed in the presence of the anti-microbial agent, thereby proving true efficacy of the anti-microbial agent, and no placebo effect.

Alternatively, the ECAR comparison may indicate no or substantially no reduction in $ECAR_1$ over time for the second sample compared to $ECAR_0$ for the first sample over the same time period, indicating that the metabolization of the bacterial sample failed to slow in the presence of the anti-microbial agent, thereby indicating there may be a placebo effect.

In some embodiments, the present invention includes a method for determining the appropriate dosage or concentration of an anti-microbial agent in an oral care composition. Specifically, the method may comprise measuring OCR at two different anti-microbial agent concentrations and determining what concentration imparts what level of anti-microbial effect to an oral care composition.

In some embodiments, any one of the methods described herein could be applied to the evaluation of certain agents useful in home care or personal care products.

In some embodiments, a second sample is prepared in a mixing step, whereby a second volume of the bacterial culture is combined with a second concentration of the first anti-bacterial agent to form a second bacterial suspension in a second container.

In other embodiments, the methods comprise a first sample and a second sample; and the first and second samples may both comprise the same type of anti-microbial agent, just at difference concentrations. With only the loading amounts of the first anti-microbial agent being different for the first and second samples, a side-by-side comparison can be made showing what dosage imparts a greater degree of anti-microbial activity in the resulting oral care composition.

In certain embodiments, the $OCR_1$ measurement of a first sample and the $OCR_2$ measurement of a second sample may occur for a predetermined period of time, referred to as a measurement cycle. In some embodiments, the measurement cycle of a first sample may be equal to the measurement cycle of a second sample.

Still further embodiments of the present invention provide methods for determining the appropriate dosage or concentration of an anti-microbial agent in an oral care composition.

Once $ECAR_1$, $ECAR_2$ values for the test sample and control sample are collected, the CPU may perform a data analysis on recorded values and generate a comparison between the extracellular acidification rate for the test sample containing the anti-bacterial agent and the control sample which may be a placebo. The ECAR comparison may indicate at relatively lower or relatively higher concentrations, the test sample imparts an improved anti-microbial efficacy.

In some embodiments, the methods comprise a harvesting step as described herein. In some embodiments, a test sample comprising a bacterial suspension is prepared by a mixing step, whereby a first volume of a bacterial suspension is combined with an anti-bacterial agent and a first oral care formulation to form a first oral care composition in a first container.

A second sample may be prepared by a mixing step, whereby a second volume of the bacterial suspension is combined with a second concentration of the anti-bacterial agent and a second oral care formulation to form a second oral care composition in a second container.

While both the first and second samples may both comprise the same anti-microbial agent and the first and second concentrations of the anti-microbial agent may be equal, the first and second oral care formulations may be different. Non-limiting examples of different oral care formulations include varying types and/or amounts of other oral-care components, such as abrasive, anti-tartar agents, whitening agents, and the like. With only the oral care formulation being different, a side-by-side comparison can be made showing how the oral care formulation impacts the degree of anti-microbial activity for a single anti-microbial agent.

Once $OCR_1$, $OCR_2$ values for the first and second samples are collected, the CPU may perform a data analysis on recorded values and generate a comparison in difference of oxygen consumption rate for different oral care composition formulations comprising the anti-bacterial agent in the first and second samples. The OCR comparison may indicate that, for a specific anti-microbial agent at a specific concentration, varying the other components in the oral care formulation may impact anti-microbial efficacy. The OCR comparison may indicate that, for a specific anti-microbial agent at a specific concentration, varying certain components in the oral care formulation may have no impact on anti-microbial efficacy.

In some embodiments, after preparing a test sample and a control sample, a sensor may contact each of the test sample and control sample; wherein the bacteria present in each sample is allowed to continue to metabolize the saccharide—during which the $ECAR_1$, $ECAR_2$ of each sample is continually measured. In some embodiments, the $ECAR_1$ measurement of the test sample and the $ECAR_2$ measurement of the control sample may run for the duration of the measurement cycle. Additionally, the span and number of cycles may be selected such as to observe a notable change in ECAR over time for at least one of the test and control samples.

Once $ECAR_1$, $ECAR_2$ values for the test sample and control sample are collected, the CPU may perform a data analysis on recorded values and generate a comparison in difference of extracellular acidification rate for a specific anti-microbial agent at a specific concentration, varying the other components in the oral care formulation may improve anti-microbial efficacy. The ECAR comparison may indicate that, for a specific anti-microbial agent at a specific concentration, varying the other components in the oral care formulation may impact anti-microbial efficacy. The ECAR comparison may indicate that, for a specific anti-microbial agent at a specific concentration, varying certain components in the oral care formulation may have no impact on anti-microbial efficacy.

Some embodiments of the present invention provide methods for identifying a composition having antimicrobial activity comprising: a) providing a bacterial biofilm; b) preparing a suspension comprising the bacterial biofilm; c) preparing a first mixture comprising the suspension comprising the bacterial biofilm, a test composition and media for culturing the bacterial biofilm; d) preparing a second mixture comprising the suspension comprising the bacterial biofilm, a control composition and media for culturing the bacterial biofilm; e) measuring the oxygen consumption rate and/or extracellular acidification rate of the first mixture and the second mixture; and f) comparing: (i) the oxygen consumption rate of the first mixture to the oxygen consumption rate of the second mixture; and/or (ii) the extracellular acidification rate of the first mixture to the extracellular acidification rate of the second mixture; wherein when the first mixture provides: a lower oxygen consumption rate compared to the second mixture; or a lower extracellular acidification rate compared to the second mixture, the test composition is identified as having antimicrobial activity. In some embodiments, the bacterial biofilm is a multi-species bacterial biofilm. Some embodiments provide methods wherein the control composition is a negative control. In some embodiments, the control composition is a positive control.

Other embodiments provide methods further comprising the step of culturing the bacterial biofilm in a medium comprising artificial saliva. In some embodiments, the medium further comprises hemin. In further embodiments, the medium further comprises menadione. Still further embodiments provide methods further comprising sucrose.

Yet other embodiments provide methods further comprising the step of harvesting the bacterial biofilm in water.

In some embodiments, the suspension comprising the bacterial biofilm is diluted to an optical density of from about 0.1 to about 0.14.

In further embodiments, the test composition is added to the first mixture in the form of a slurry. In certain embodiments, the slurry comprises the test composition and water in a w/w ratio of from about 1:10 to about 1:50.

Still further embodiments provide methods further comprising the step of centrifuging the first mixture. Yet other embodiments provide methods further comprising the step of centrifuging the second mixture. In some embodiments, the centrifuging is done for about ten (10) minutes at about 1,500×g. In further embodiments, the centrifuging is done under ambient conditions.

Other embodiments provide methods further comprising the step of equilibrating the second mixture before measuring the oxygen consumption rate and/or extracellular acidification rate of the second mixture. In some embodiments, an equilibration step is not performed before measuring the oxygen consumption rate and/or extracellular acidification rate of the first mixture.

In some embodiments, the methods further comprise the step of adding the first mixture to a microwell plate. While other embodiments further comprise the step of adding the second mixture to a microwell plate.

In some embodiments, the oxygen consumption rate and/or extracellular acidification rate are measured over about ten (10) to about one hundred (100) cycles. In further embodiments, the oxygen consumption rate and/or extracellular acidification rate are measured over about twenty-five (25) to about seventy-five (75) cycles. While in other embodiments, the oxygen consumption rate and/or extracellular acidification rate are measured over about fifty (50) cycles. In some embodiments, area under the curve (AUC) is calculated during and/or after the cycles are completed.

In some embodiments, the test composition comprises an ingredient selected from: a zinc ion source; a stannous ion source; a fluoride ion source; a peroxide source; a basic amino acid; and a combination of two or more thereof. In further embodiments, the test composition comprises a zinc ion source and/or a basic amino acid. In some embodiments, the test composition comprises a stannous ion source.

In some embodiments, the control composition comprises a zinc ion source or a fluoride ion source. In other embodiments, the control composition consists essentially of a zinc ion source or a fluoride ion source. While in other embodiments, the control composition consists of a zinc ion source or a fluoride ion source.

In some embodiments, the zinc ion source comprises zinc oxide and/or zinc citrate.

In some embodiments, the bacterial biofilm is not pretreated.

In some embodiments, the first mixture has an optical density of from about 0.05 to about 0.07. In other embodiments, the second mixture has an optical density of from about 0.05 to about 0.07.

In some embodiments, the test composition comprises a zinc ion source and the slurry comprises the test composition and water in a w/w ratio of about 1:10. In other embodiments, the test composition comprises a stannous ion source and the slurry comprises the test composition and water in a w/w ratio of about 1:50.

In further embodiments, the first mixture has a volume of from about 100 microliters (μL) to about 500 microliters (μl). In other embodiments, the first mixture has a volume of from about 150 microliters (μL) to about 450 microliters (μl). In some embodiments, the first mixture has a volume of from about 150 microliters (μL) to about 400 microliters (μl). In certain embodiments, the first mixture has a volume of from about 150 microliters (μL) to about 350 microliters (μl). While in other embodiments, the first mixture has a volume of from about 175 microliters (μL) to about 300 microliters (μl). Still further embodiments provide a first mixture having a volume of from about 175 microliters (μL) to about 250 microliters (μl). In other embodiments, the first mixture has a volume of about 200 microliters (μL).

Still further embodiments provide systems for: identifying a composition having anti-pathogenic activity; evaluating the anti-pathogenic activity of a composition; measuring the metabolic function of a pathogen; and/or comparing the anti-pathogenic performance of a plurality of compositions; wherein the system comprises: a specimen comprising a pathogen; a test sample comprising the specimen, a test composition and media for culturing the specimen; a control sample comprising the specimen, a control composition and media for culturing the specimen; a plurality of microwell plates; and an apparatus comprising: at least one optical sensor; and a processor.

In some embodiments, the pathogen is selected from: a bacterium; a fungus; and a combination of two or more thereof. In some embodiments, the pathogen is selected from *Actinomyces; Arachnia, Bateroides, Bifidobacterium; Eubacterium; Fusobacterium; Lactobacillus; Leptotrichia; Peptococcus; Streptococcus; Peptostreptococcus; Propionibacterium; Selenomonas; Treponema; Veillonella; Neisseria; Prevotella; Candida; Aggregatibacter*; and a combination of two or more thereof. In some embodiments, the *Candida* is *C. albicans*.

In further embodiments, the pathogen comprises a bacterial biofilm. In other embodiments, the bacterial biofilm is a multi-species bacterial biofilm.

In some embodiments, the optical sensor is configured to measure an oxygen consumption rate and/or an extracellular acidification rate of the test sample. In further embodiments, an optical sensor measures an oxygen consumption rate and/or an extracellular acidification rate of the control sample. Still further embodiments provide systems wherein the optical sensor is configured to transmit information to the processor. In some embodiments, the optical sensor is in wireless communication with the processor. In certain embodiments, the oxygen consumption rate and/or extracellular acidification rate of the test sample and the oxygen consumption rate and/or extracellular acidification rate of the control sample are transmitted to the processor. In some embodiments, the oxygen consumption rate and/or an extracellular acidification rate is used to calculate the metabolic function of a pathogen.

In some embodiments, the oxygen consumption rates and extracellular acidification rates of the test sample and the control sample are plotted. In further embodiments, the processor is configured to calculate area under the curve for the oxygen consumption rate curve and the extracellular acidification rate curve for the test sample and the control sample. While in other embodiments, when the area under the oxygen consumption rate curve for the test sample is less than the area under the oxygen consumption rate curve for the control sample, the test sample has anti-pathogenic activity. In other embodiments, when the area under the extracellular acidification rate curve for the test sample is less than the area under the extracellular acidification rate curve for the control sample, the test sample has anti-pathogenic activity.

Still further embodiments provide methods for evaluating the antimicrobial activity of a composition comprising: a) providing a multi-species bacterial biofilm; b) preparing a suspension comprising the bacterial biofilm; c) providing a test composition and a control composition; d) providing media for culturing the bacterial biofilm; e) preparing a first mixture comprising the suspension comprising the bacterial biofilm, the test composition and the media for culturing the bacterial biofilm; f) preparing a second mixture comprising the suspension comprising the bacterial biofilm, the control composition and the media for culturing the bacterial biofilm; and g) measuring the oxygen consumption rate and/or extracellular acidification rate of the first mixture and the second mixture. In some embodiments, steps a) to g) are repeated three (3) times.

Other embodiments provide methods wherein the oxygen consumption rates and extracellular acidification rates of the first mixture and the second mixture are plotted and the area under the oxygen consumption rate curve and area under the extracellular acidification rate curve for the first mixture and the second mixture are calculated. While other embodiments provide methods wherein when the area under the extracellular acidification rate curve for the first mixture is less than the area under the extracellular acidification rate curve for the second mixture, or the area under the oxygen consumption rate curve for the first mixture is less than the area under the oxygen consumption rate curve for the second mixture, the first mixture has antimicrobial activity.

In some embodiments, the present invention includes the step of formulating a product based on the results obtained from any one of the methods described herein. In some embodiments, the product is a personal care product. A personal care product may exist for enhancing a user's health, hygiene, appearance, etc. Such personal care products may comprise one or more chemical compositions that are comprised of one or more ingredients. Personal care products may include oral care products comprising oral care compositions, skin care products comprising skin care compositions, hair care products comprising hair care compositions, as well as other products and/or chemical compositions.

Oral care composition, as used herein, may include a composition for which the intended use can include oral care, oral hygiene, oral appearance, or for which the intended use may comprise administration to the oral cavity. Skin care composition, as used herein, may include a composition for which the intended use may include promotion or improvement of health, cleanliness, odor, appearance, and/or attractiveness of skin. Hair care compositions, as used herein, may include a composition for which the intended use may include promotion or improvement of health, cleanliness, appearance, and/or attractiveness of hair. The compositions may be used for a wide variety of purposes, including for enhancing personal health, hygiene, and appearance, as well as for preventing or treating a variety of diseases and other conditions in humans and in animals.

Although several embodiments of the invention have been disclosed in the foregoing specification, it is understood by those skilled in the art that many modifications and other embodiments of the invention will come to mind to which the invention pertains, having the benefit of the teaching presented in the foregoing description and associated drawings. It is thus understood that the invention is not limited to the specific embodiments disclosed hereinabove, and that many modifications and other embodiments are intended to be included within the scope of the appended claims. Moreover, although specific terms are employed herein, as well as in the claims which follow, they are used only in a generic and descriptive sense, and not for the purposes of limiting the described invention, nor the claims which follow.

What is claimed is:

1. A method for identifying a composition having antimicrobial activity comprising:
   a) culturing a bacterial biofilm in a medium comprising artificial saliva, hemin, menadione and/or sucrose;
   b) harvesting the bacterial biofilm in water to form a suspension comprising the bacterial biofilm;
   c) preparing a first mixture comprising the suspension comprising the bacterial biofilm, a test composition and media for culturing the bacterial biofilm;
   d) preparing a second mixture comprising the suspension comprising the bacterial biofilm, a control composition and media for culturing the bacterial biofilm;
   e) measuring the oxygen consumption rate and/or extracellular acidification rate of the first mixture and the second mixture; and
   f) comparing:
      (i) the oxygen consumption rate of the first mixture to the oxygen consumption rate of the second mixture; and/or
      (ii) the extracellular acidification rate of the first mixture to the extracellular acidification rate of the second mixture;
   wherein when the first mixture provides:
   a lower oxygen consumption rate compared to the second mixture; or
      a lower extracellular acidification rate compared to the second mixture, the test composition is identified as having antimicrobial activity;
   wherein the composition is an oral care composition.

2. The method according to claim 1, wherein the suspension comprising the bacterial biofilm is diluted to an optical density of from about 0.1 to about 0.14.

3. The method according to claim 1, further comprising the step of centrifuging the first mixture and the second mixture after step d) but before step e) for about ten (10) minutes at about 1,500×g under ambient conditions.

4. The method according to claim 3, further comprising the step of equilibrating the second mixture before measuring the oxygen consumption rate and/or extracellular acidification rate of the second mixture.

5. The method according to claim 4, further comprising the step of adding the first mixture and second mixture to a microwell plate.

6. The method according to claim 1, wherein the oxygen consumption rate and/or extracellular acidification rate are measured over about ten (10) to about one hundred (100) cycles.

7. The method according to claim 6, wherein area under the curve (AUC) is calculated during and/or after the cycles are completed.

8. The method according to claim 1, wherein the test composition comprises an ingredient selected from: a zinc ion source; a stannous ion source; a fluoride ion source; a peroxide source; a basic amino acid; and a combination of two or more thereof.

9. The method according to claim 1, wherein the control composition comprises a zinc ion source or a fluoride ion source.

10. The method according to claim 1, wherein the bacterial biofilm is not pretreated.

11. The method according to claim 1, wherein the first mixture has an optical density of from about 0.05 to about 0.07 and/or the second mixture has an optical density of from about 0.05 to about 0.07.

12. A method for evaluating the antimicrobial activity of a composition comprising:
   a) providing a multi-species bacterial biofilm;
   b) harvesting the bacterial biofilm in water to form a suspension comprising the bacterial biofilm;
   c) providing a test composition and a control composition;
   d) providing media for culturing the bacterial biofilm;

e) preparing a first mixture comprising the suspension comprising the bacterial biofilm, the test composition and the media for culturing the bacterial biofilm;

f) preparing a second mixture comprising the suspension comprising the bacterial biofilm, the control composition and the media for culturing the bacterial biofilm; and g) measuring the oxygen consumption rate and/or extracellular acidification rate of the first mixture and the second mixture;

wherein the composition is an oral care composition.

13. The method according to claim 12, wherein the method is repeated three (3) times.

* * * * *